United States Patent [19]

Beitzke et al.

[11] Patent Number: 4,613,692

[45] Date of Patent: Sep. 23, 1986

[54] PROCESS FOR THE PREPARATION OF CINNAMIC ACIDS WHICH ARE OPTIONALLY SUBSTITUTED IN THE NUCLEUS

[75] Inventors: Bernhard Beitzke, Bergisch Gladbach; Volkmar Handschuh, Burscheid; Heinz U. Blank, Odenthal, all of Fed. Rep. of Germany

[73] Assignee: Bayer Aktiengesellschaft, Leverkusen, Fed. Rep. of Germany

[21] Appl. No.: 743,254

[22] Filed: Jun. 11, 1985

[30] Foreign Application Priority Data

Jun. 20, 1984 [DE] Fed. Rep. of Germany ....... 3422915

[51] Int. Cl.$^4$ .............................................. C07C 63/64
[52] U.S. Cl. .................................... 562/495; 560/104
[58] Field of Search ......................... 562/495; 560/104

[56] References Cited

PUBLICATIONS

The Journal of Organic Chemistry, Band 15, No. 3, May 1950, pp. 451–456, J. F. J. Dippy and R. M. Evans, "The Nature of the Catalyst in the Perkin Condensation".

Primary Examiner—Paul J. Killos
Attorney, Agent, or Firm—Sprung Horn Kramer & Woods

[57] ABSTRACT

A process for the preparation of cinnamic acid is provided by the present invention in which an optionally substituted benzaldehyde and alkali metal salt of carboxylic acid and/or alkali metal (bi) carbonate, as condensing agents, are heated up to a temperature of 100°–220° C. and thereafter there is introduced into the so heated mixture acetic anhydride in at least a stoichiometric amount based upon the amount of optionally substituted benzaldehyde employed. The process can be carried out by heating up a reaction mixture to 100°–220° C. which is free of acetic anhydride or one which contains acetic anhydride but less than a stoichiometric amount thereof based upon the amount of optionally substituted benzaldehyde.

14 Claims, No Drawings

PROCESS FOR THE PREPARATION OF CINNAMIC ACIDS WHICH ARE OPTIONALLY SUBSTITUTED IN THE NUCLEUS

The present invention relates to an improved process for the preparation of cinnamic acids which are optionally substituted in the nucleus, by the Perkin reaction, from an optionally substituted aromatic aldehyde, acetic anhydride and alkaline condensing agents.

The Perkin reaction is known per se (Houben-Weyl, 4th edition, volume VIII, pages 442 et seq. (1952); Org. React. I, pages 210-265 (1942); Ullmanns Enzyklopädie der technischen Chemie (Ullmann's Encyclopaedia of Industrial Chemistry), 3rd edition, volume 19, page 36 (1969)). It entails all the reactants being mixed and heated under reflux together for a prolonged period, where appropriate the resulting acetic acid being removed by distillation. The condensing agent mentioned in German Offenlegungsschrift No. 1,568,184 is sodium acetate/potassium acetate mixed with potassium carbonate/potassium bicarbonate, and a reaction temperature of 130°-200° C. is mentioned.

In this process due to side reactions, dark-brown resins are produced, and these make it necessary to extract the cinnamate solution with an organic solvent and/or to clarify it with active charcoal. Nevertheless, the cinnamic acid obtained after these purification operations, unless carried out several times, is discoloured yellow or brownish. Thus the effort involved in the preparation of a colourless cinnamic acid is considerable.

Cinnamic acid is a precursor for the preparation of L-phenylalanine which is prepared from the acid by enzymatic amination (Chem. Abstr. 89, 213 580p (1978), Chem. Abstr. 95, 95 470b (1981)). A particularly pure cinnamic acid, which must be free of coloured impurities, is required for this biotransformation.

As an improvement of the process of preparation, subsequent metering in of potassium carbonate during the reaction is described in German Offenlegungsschrift No. 3,139,994.

According to the statements in German Offenlegungsschrift No. 3,144,261 a purer final product is obtained in the Perkin reaction when the acetic anhydride is first enolised by heating with the condensing agent, and then the aldehyde is allowed to run in at a constant rate during the reaction time.

However, it has been found, suprisingly, that the side reactions and the resin formation can be suppressed to a considerable extent if, in contrast to the teaching of German Offenlegungsschrift No. 3,144,261, the acetic andride is metered into the benzaldehyde which has been initially introduced.

A process for the preparation of cinnamic acid is provided by the present invention in which an optionally substituted benzaldehyde and alkali metal salt of carboxylic acid and/or alkali metal (bi) carbonate, as condensing agents, are heated up to a temperature of 100°-220° C. and thereafter there is introduced into the so heated mixture acetic anhydride in at least a stoichiometric amount based upon the amount of optionally substituted benzaldehyde employed. The process can be carried out by heating up a reaction mixture to 100°-220° C. which is free of acetic anhydride or one which contains acetic anhydride but less than a stoichiometric amount thereof based upon the amount of optionally substituted benzaldehyde.

Starting materials for the process according to the invention which may be mentioned are aromatic aldehydes of the formula

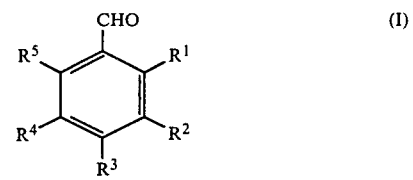

in which
  $R^1$ denotes hydrogen, halogen or alkyl,
  $R^2$, $R^3$ and $R^4$, independently of one another, denote hydrogen, halogen, alkyl, aryl or aryloxy, and
  $R^5$ denotes hydrogen or halogen,
and wherein further
  up to four of any radicals $R^1$ to $R^5$ may denote alkoxy,
  up to two of any radicals $R^1$ to $R^5$ may denote nitro, and
  up to two of any radicals $R^2$ to $R^4$ may denote cyano and/or alkoxycarbonyl.

In a preferred manner, aromatic aldehydes of the formula

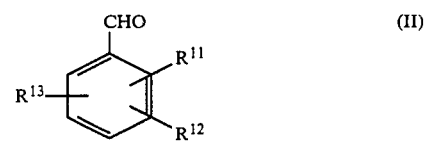

are used in which
  $P^{11}$, $R^{12}$ and $R^{13}$, independently of one another, denote hydrogen, halogen, alkyl, aryl, aryloxy or alkoxy,
  wherein in the case of alkyl one of the ortho-positions of the aldehyde group denotes hydrogen, and in the case of aryl both ortho-positions of the aldehyde group denote hydrogen,
and wherein further
  up to two of any radicals $R^{11}$ to $R^{13}$, independently of one another, denote trifluoromethyl, nitro, cyano or alkoxycarbonyl wherein in the case of cyano or alkoxycarbonyl both the ortho-positions of the aldehyde group denote hydrogen.

In a particularly preferred manner, aromatic aldehydes of the formula

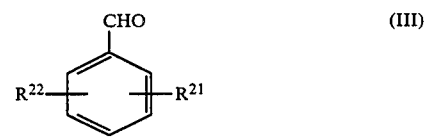

are used in which
  $R^{21}$ and $R^{22}$, independently of one another, denote hydrogen, halogen, aryl, aryloxy, alkoxy or nitro, wherein in the case of aryl and aryloxy both the ortho-positions of the aldehyde group denote hydrogen.

In a very particularly preferred manner, aromatic aldehydes of the formula

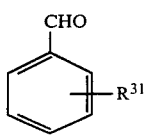 (IV)

in which

R³¹ represents hydrogen or halogen are used.

Examples of halogen which may be mentioned are fluorine, chlorine, bromine or iodine, preferably fluorine, chlorine or bromine, particularly preferably fluorine or chlorine.

Examples of alkyl which may be mentioned are straight-chain or branched or cyclic hydrocarbon radicals having 1–10 C atoms (cyclic with 4–8 C atoms), preferably having 1–6 C atoms (cyclic with 5–6 C atoms); in a preferred manner, straight-chain or branched hydrocarbon radicals without a cyclic structure, in this connection especially those having 1–6 C atoms, may be mentioned. Alkyl includes according to the inventive process hydrocarbon radicals which are single- or multiple-substituted with fluorine, preferred $C_1$–$C_6$ fluorine-substituted hydrocarbon radicals, especially preferred trifluoromethyl.

Examples of aryl which may be mentioned are phenyl, naphthyl, anthryl and biphenylyl, preferably phenyl, which can be single- or multiple-substituted with methyl, ethyl or halogen.

The alkyl and aryl groups in the alkoxy, alkoxycarbonyl and aryloxy substituents have the range of meaning mentioned.

Examples of aromatic aldehydes which are to be reacted according to the invention and which may be mentioned are: benzaldehyde, nitrobenzaldehyde (o, m, p), methoxybenzaldehyde (o, m, p), 4-phenylbenzaldehyde, phenoxybenzaldehyde (o, m, p), chlorobenzaldehyde (o, m, p) and fluorobenzaldehyde (o, m, p).

The condensing agents used are: alkali metal salts of carboxylic acids, for example sodium formate, potassium formate, sodium acetate, potassium acetate or alkali metal (bi)carbonates, such as, for example, sodium carbonate, potassium carbonate, rubidium carbonate or cesium carbonate, and the respective bicarbonates. Of course, it is possible to use mixtures of these condensing agents. In general, the amount of the condensing agent is 0.1–1.5 equivalents of alkali metal cation per mole of benzaldehyde, preferably 0.3–1.3 equivalents, particularly preferably 0.5–1.1 equivalents. In a preferred manner, a mixture of $Na^+$ ions and ions of the heavy alkali metals is used, for example sodium acetate/potassium (bi)carbonate or sodium acetate/potassium acetate, it being possible to replace, partly or completely, the potassium salt by salts of rubidium and/or cesium.

In a mixture of this type, the heavy alkali metal is present to the extent of, for example, 5–50 equivalent-%, preferably 10–40 equivalent-%, based on the total amount of alkali metal equivalents.

The reaction of the process according to the invention is carried out such that the optionally substituted benzaldehyde and the condensing agent (optionally a mixture) are initially introduced into a reaction vessel, optionally in the presence of a less than stoichiometric amount of acetic anhydride, are heated to the selected reaction temperature, and then the remaining amount of the acetic anhydride is metered in and, where appropriate, heating is continued to the end of the reaction or, where appropriate, the temperature is raised within the scope of the range mentioned.

The amount of acetic anhydride which is initially introduced together with the benzaldehyde and the condensing agent(s) can be between 0 and 75 mole-%, based on the aldehyde. The amount of acetic anhydride which is initially introduced is preferably 0–50, particularly preferably 0–30, mole-%. For example, good results are obtained when 0.1–0.3 mole acetic anhydride per mole of benzaldehyde is initially introduced.

The amount of acetic anhydride which is to be metered is the difference between the amount which is initially introduced and the total amount of 1–1.5 mole of acetic anhydride per mole of the optionally substituted benzaldehyde. In a preferred manner, the total amount of acetic anhydride is 1.0–1.4 mole, and in a particularly preferred manner it is 1.1–1.3 mole, per mole of the optionally substituted benzaldehyde.

In the case where alkali metal (bi)carbonates are used, part of the acetic anhydride is consumed, for example in accordance with the equation

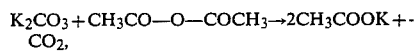

This amount of acetic anhydride consumed is not included in the total amount mentioned, and must be added where appropriate.

In order to suppress the formation of resin in the manner according to the invention, it suffices, after heating the mixture which has been initially introduced, to meter in the acetic anhydride, in the first part of the overall reaction time. Examples of the first part of the overall reaction time which may be mentioned are the first tenth or the first eighth; however, it is of course also possible to meter in the acetic anhydride throughout the entire duration of the reaction time. It is possible for this to entail the acetic anhydride first being added at a relatively high rate of metering and to be added in the subsequent course of the reaction at a lower rate of metering. However, the acetic anhydride which is to be metered in can also be metered in at a constant rate until the intended total amount of acetic anhydride is reached. Thus, for example with an overall reaction time of 8 hours, the reaction mixture obtained when, according to the invention, the acetic anhydride is metered in at a constant rate in the first hour, and then heating under reflux is continued for 7 hours, has a markedly lighter colour than when, according to the state of the art, all the reactants are heated under reflux together for 8 hours.

The procedure according to the invention can be operated both under reflux and with removal of acetic acid by distillation. If it is intended to remove the acetic acid of reaction by distillation, then the acetic anhydride is metered in as slowly as possible; this results in the bottom concentration of acetic anhydride being kept small and the removal of the acetic acid by distillation facilitated.

The reaction according to the invention is carried out in a temperature range of 100°–220° C., preferably 140°–210° C., particularly preferably 150°–190° C. It is advantageous to heat the mixture which has been initially introduced and comprises the benzaldehyde and condensing agent(s) and, where appropriate, part of the acetic anhydride to the reflux temperature, and then to meter in the remaining acetic anhydride. Thus, for example, the metering in of the acetic anhydride can be carried out at a bottom temperature of 150°–165° C.

In a particularly preferred procedure, a mixture of the optionally substituted benzaldehyde and 10–30 mole-% of acetic anhydride (based on the aldehyde), together with the condensing agent(s) is initially introduced, and this mixture is reacted at 100°–165° C., and then, at a bottom temperature between 150° and 200° C., the remaining acetic anhydride is metered in during the course of the reaction until a molar ratio of 1 to 1.5 mole of acetic anhydride per mole of (substituted) benzaldehyde is reached. The mixture is then heated until no further conversion is detectable. This can be established by chromatographic methods (gas chromatography or high-pressure liquid chromatography).

An advantage of the procedure according to the invention comprises the possibility of starting at a high bottom temperature, which is above the boiling point of acetic anhydride, by which means a high reaction rate is achieved. It is possible thus to achieve high yields in a short time.

The reaction can be carried out both under atmospheric pressure and under elevated pressure. It is advantageous to operate under elevated pressure in the upper part of the temperature range indicated, the metering in of the acetic anhydride being carried out by, for example, pumping in.

The reaction should be carried out under a protective gas, for example nitrogen.

It has to be denoted extremely surprising that the formation of by-products and resin can be essentially prevented by the procedure, according to the invention, of metering in acetic anhydride, while expressly the reverse procedure is described in German Offenlegungsschrift No. 3,144,261 to achieve the same object. It is particularly surprising that it suffices to meter in the acetic anhydride during a first part of the overall reaction time in order to achieve the marked effects of suppression of the formation of by-products and resin (that is to say a considerable improvement in colour).

The process according to the invention makes it possible a) essentially to suppress the formation of resin, b) associated with this, to simplify, shorten and reduce the cost of work-up, c) to remove the acetic acid of reaction by distillation more readily and d) to shorten the reaction times due to the higher bottom temperatures from the start of the reaction.

EXAMPLE 1

106.1 g of benzaldehyde, 61 g of sodium acetate and 18 g of potassium carbonate were initially introduced into a 2 litre flask with stirrer, reflux condenser, thermometer and dropping funnel, and were heated to 160° C. Then 136 g of acetic anhydride were added dropwise at a constant rate within 80 minutes. The mixture was then heated under reflux for 6 hours and 40 minutes. A sample of 27.1 g of the reaction mixture thus obtained exhibited, as a 10% by weight solution in glacial acetic acid, a Hazen number of 350 (APHA). The volatile constituents were then removed by distillation (111 g). 700 ml of water and 250 ml of toluene were added to the residue. The aqueous phase was adjusted to pH 8, and then the phases were separated. Extraction was repeated twice more with 200 ml of toluene each time, and then the cinnamic acid was isolated from the aqueous phase by acidification. 96.6 g of cinnamic acid with a Hazen number of 200 (APHA), measured as a 10% by weight solution in glacial acetic acid, were obtained. The purity of the cinnamic acid was more than 99%.

EXAMPLE 2

The process was carried out as in Example 1, but the heating under reflux after the dropwise addition of the acetic anhydride lasted only 5 hours 40 minutes. The reaction mixture was pale yellow after this. After working up as in Example 1, 104 g of cinnamic acid, melting point 135°–136.5° C., were obtained; this corresponded to 70% of the theoretical yield. The product had a Hazen number of 200.

EXAMPLE 3

(Comparison Example)

The same amounts as in Example 1 were used, but all the reactants were mixed together, heated and refluxed for 8 hours. After this, a sample of the reaction mixture (measured as in Example 1) had a Hazen number above 500 (number on the iodine scale 30, and Gardner number 9).

EXAMPLE 4

318.4 g of benzaldehyde, 182 g of sodium acetate and 47 g of potassium carbonate were initially introduced into a 2 litre four-necked flask with stirrer, thermometer, dropping funnel (500 ml) with facility for passing $N_2$ over, and distillation device, and were heated to 165° C. At a constant bottom temperature of 165° C., 385 ml (408 g) of acetic anhydride were added dropwise at a constant rate within 260 min. After the addition of about 150 ml of acetic anhydride, reflux at the top of the column started, and a distillate was removed under normal pressure and at an overhead temperature of 117° C. (maximum 118.5° C.). After the end of the addition of the acetic anhydride, removal of distillate was continued for as long as this was possible at a bottom temperature of 165° (about 15 min.). A sample from the reaction mixture had a Hazen number of 350 (APHA) determined in the manner indicated above. After working up in analogy to Example 1, 318.1 g of cinnamic acid, purity 99.6 %, were obtained. This corresponded to a yield of 71.3 % of the theoretical yield based on the charge of benzaldehyde. The product had a Hazen number of 200 measured as a 10% strength solution in acetic acid.

EXAMPLE 5

318.4 g of benzaldehyde, 102 g of acetic anhydride, 182 g of sodium acetate and 54 g of potassium carbonate were initially introduced into an apparatus as described in Example 1, and were heated to 150° C. and maintained at this temperature for 30 min. The mixture was then heated to 155°–160° C. and 306.4 g of acetic anhydride were metered in so that the bottom temperature did not fall below 157° C. The overall reaction time was 8 h.

A sample from the reaction mixture had a Hazen number of 400 determined in the manner indicated above. After working up in analogy to Example 1, 300 g of cinnamic acid of melting point 135°–136° C. were obtained.

What is claimed is:

1. A process for the preparation of a cinnamic acid which comprises introducing into a reaction vessel an optionally substituted benzaldehyde and an alkali metal salt of a carboxylic acid and/or alkali metal (bi) carbonate, the resultant mixture containing less than a stoichiometric amount of acetic anhydride, heating the reaction mixture to a temperature in the range of 100° to 200° C. and thereafter adding sufficient acetic anhydride such that it is present in at least a stoichiometric amount based upon the amount of optionally substituted benzaldehyde, the acetic anhydride being at least partially metered in during the course of reaction of the optionally substituted benzaldehyde with acetic anhydride.

2. A process according to claim 1 wherein the reaction mixture which is heated up to a temperature of 100° to 220° C. is free of acetic anhydride.

3. A process according to claim 1 wherein the reaction mixture which is heated up to 100° to 200° C. contains acetic anhydride but in a less than stoichiometric amount based upon the amount of optionally substituted benzaldehyde.

4. A process according to claim 1 wherein said optionally substituted benzaldehyde is one of the formula

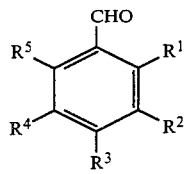

in which
R$^1$ denotes hydrogen, halogen or alkyl,
R$^2$, R$^3$ and R$^4$, independently of one another, denote hydrogen, halogen, alkyl, aryl or aryloxy, and
R$^5$ denotes hydrogen or halogen,
and wherein further
up to four of any radicals R$^1$ to R$^5$ may denote alkoxy,
up to two of any radicals R$^1$ to R$^5$ may denote nitro, and
up to two of any radicals R$^2$ to R$^4$ may denote cyano and/or alkoxycarbonyl.

5. A process according to claim 3 wherein the acetic anhydride is present in an amount of up to 75 mole percent based on the optionally substituted benzaldehyde.

6. A process according to claim 3 wherein the acetic anhydride is present in an amount of up to 50 mole percent based upon the optionally substituted benzaldehyde.

7. A process according to claim 3 wherein the acetic anhydride is present in an amount of up to 30 mole percent based upon the optionally substituted benzaldehyde.

8. A process according to claim 3 wherein the acetic anhydride is present in an amount of 10 to 30 mole percent based upon the amount of the optionally substituted benzaldehyde.

9. A process according to claim 1 wherein the total amount of acetic anhydride employed is 1.0-1.5 mole acetic anhydride per mole of optionally substituted benzaldehyde.

10. A process according to claim 9 wherein the acetic anhydride is employed in a molar ratio of 1.0 to 1.4 moles acetic anhydride per mole of optionally substituted benzaldehyde.

11. A process according to claim 1 wherein the acetic anhydride is employed in an amount of 1.1-1.3 moles per mole of optionally substituted benzaldehyde.

12. A process according to claim 1 wherein the alkali metal of carboxylic acid and/or alkali metal (bi) carbonate is a salt mixture containing sodium ions and ions of heavier alkali metals in which the ions of the heavier alkali metals constitute 5 to 50 mole equivalents of the total amount of alkali metal ions in said alkali metal salts of carboxylic acids or alkali metal (bi) carbonates.

13. A process according to claim 1 wherein the reaction mixture which is initially heated to 100°-220° C. is heated to a temperature of 100°-165° C. and comprises said optionally substituted benzaldehyde, alkali metal acetate and/or alkali metal carbonate and an amount of acetic anhydride of 10 to 30 mole percent based upon the amount of said optionally substituted benzaldehyde and after the reaction has achieved a temperature of 100°-165° C. the remaining acetic anhydride is metered in during the course of reaction while the reaction mixture is maintained at a temperature of 150°-220° C., the total amount of acetic anhydride being employed being 1-1.5 moles of acetic anhydride per mole of optionally substituted benzaldehyde.

14. A process according to claim 1 wherein the reaction mixture comprises benzaldehyde.

* * * * *